(12) United States Patent
Bevill et al.

(10) Patent No.: US 9,314,459 B2
(45) Date of Patent: Apr. 19, 2016

(54) POLYMORPHS OF COCRYSTALS OF P-COUMARIC ACID:NICOTINAMIDE

(71) Applicant: AMRI SSCI, LLC, West Lafayette, IN (US)

(72) Inventors: Melanie Janelle Bevill, West Lafayette, IN (US); Nate Schultheiss, Kingwood, TX (US)

(73) Assignee: AMRI SSCI, LLC, West Lafayette, IN (US)

(*) Notice: Subject to any disclaimer, the term of this patent is extended or adjusted under 35 U.S.C. 154(b) by 0 days.

(21) Appl. No.: 14/607,186

(22) Filed: Jan. 28, 2015

(65) Prior Publication Data

US 2015/0216851 A1 Aug. 6, 2015

Related U.S. Application Data

(60) Provisional application No. 61/935,570, filed on Feb. 4, 2014.

(51) Int. Cl.
 *A61K 31/44* (2006.01)
 *A61K 31/455* (2006.01)
 *A61K 31/192* (2006.01)

(52) U.S. Cl.
 CPC .............. *A61K 31/455* (2013.01); *A61K 31/192* (2013.01)

(58) Field of Classification Search
 CPC .................................................... A61K 31/192
 USPC ......................................................... 514/357
 See application file for complete search history.

(56) References Cited

U.S. PATENT DOCUMENTS

| | | | |
|---|---|---|---|
| 7,452,555 B2 | 11/2008 | Childs | |
| 8,212,079 B2 | 7/2012 | Childs | |
| 8,350,085 B2 | 1/2013 | Childs | |
| 9,120,766 B2 | 9/2015 | Bevill et al. | |
| 2011/0251426 A1 | 10/2011 | Childs et al. | |
| 2013/0102781 A1* | 4/2013 | Bevill et al. | 544/323 |
| 2014/0073674 A1 | 3/2014 | Bevill et al. | |
| 2014/0235595 A1 | 8/2014 | Albert et al. | |

OTHER PUBLICATIONS

Breuil, A.C. et al., "Characterization of a Pterostilbene Dehydrodimer Produced by Laccase of Botrytis cinerea," Phytopathology vol. 89, No. 4, pp. 298-302 (1999).
Etter, Margaret C. et al., "Graph-Set Analysis of Hydrogen-Bond Patterns in Organic Crystals," Acta Cryst., B46, pp. 256-262 (1990).
Etter, Margaret C. et al., "The Use of Cocrystallization as a Method of studying Hydrogen Bond Preferences of 2-Aminopyridine," Journal of the Chemical Society, Chemical Communications, No. 8, pp. 589-591 (1990).
Flack, H.D., "On Enantiomorph-Polarity Estimation," Acta Cryst., A39, pp. 876-881 (1983).
Gorbitz, C.H. et al., "On the inclusion of solvent molecules in the crystal structures of organic compounds," Acta Cryst., B56, pp. 526-534 (2000).
Hooft, R.W.W. et al., "Determination of absolute structure using Bayesian statistics on Bijvoet differences", J. Appl. Cryst., vol. 41, pp. 96-103 (2008).
Kumar et al., "Molecular Complexes of Some Mono- and Dicarboxylic Acids with trans-1,4-Dithiane-1,4-dioxide," American Chemical Society, Crystal Growth & Design, vol. 2, No. 4, pp. 313-318 (2002).
Pezet, R., "Purification and characterization of a 32-kDa laccase-like stilbene oxidase produced by Botrytis cinerea Pers.:Fr.," FEMS Microbiology Letters, vol. 167, pp. 203-208 (1998).
Schultheiss, N. et al., "Nutraceutical cocrystals: utilizing pterostilbene as a cocrystal former," Crystal Engineering Communications, vol. 12, pp. 2436-2442 (2010).
Schultheiss, N. et al., "Attempted construction of minoxidil: carboxylic acid cocrystals; 7 salts and 1 cocrystal resulted," Crystal Engineering Communications, vol. 12, pp. 742-749 (2010).
Schultheiss, N. et al., "Attempted construction of minoxidil: carboxylic acid cocrystals; 8 salts and 1 cocrystal resulted," Crystal Engineering Communications, Supplementary Material, pp. 1-19 (2010).
Schultheiss, N. et al., "Nifedipine—pyrazine (2/1)," Acta Cryst. E66, pp. o2297-o2298 and Sup-1 to Sup-9 (2010).
David C. Lee and Michael L. Webb, Pharmaceutical Analysis, 2003, pp. 254-259, 1st edition, CRC Press, Boca Raton, Florida, United States of America.
Nate Schultheiss, et al, "Cocrystals of nutraceutical p-coumaric acid with caffeine and theophylline: polymorphism and solid-state stability explored in detail using their crystal graphs," CrystEngComm, vol. 13, pp. 611-619 (2011) The Royal Society of Chemistry, London, United Kingdom.
Ivanisevic et al., "Uses of X-Ray Powder Diffraction in the Pharmaceutical Industry," Pharmaceutical Sciences Encyclopedia: Drug Discovery, Development, and Manufacturing, pp. 1-42 (2010).
Ivanisevic et al., "Uses of X-Ray Powder Diffraction in the Pharmaceutical Industry," Pharm. Form Qual. pp. 30-33 (2011).
Bhattacharya et al. "Thermoanalytical and Crystallographic Methods" in Brittain H. ed. 2nd ed. Informa Healthcare:NY, pp. 318-335 (2009).
Aakeroy, "Crystal Engineering: Strategies and Architectures ," Acta Cryst. B53, pp. 569-586 (1997).
Sekhon BS, "Pharmaceutical co-crystals—a review," Ars Pharm. 50(3): 99-117 (2009).
Kirk-Othmer Encyclopedia of Chemical Technology, 8, pp. 95-147 (2002).
Haleblian et al., "Pharmaceutical Applications of Polymorphism," Journal of Pharmaceutical Sciences 58(8), pp. 911-929 (1969).
Bernstein, "Polymorphism in Molecular Crystals," pp. 115-118 and 272 (2002).

(Continued)

Primary Examiner — Nizal Chandrakumar
(74) Attorney, Agent, or Firm — LeClairRyan, a Professional Corporation

(57) ABSTRACT

Polymorphs, Forms II and III, of cocrystals of p-coumaric acid and nicotinamide in a 1:1 molar ratio. Pharmaceutical compositions containing Forms II or III, processes for making such forms, and methods of treatment with such Forms.

8 Claims, 6 Drawing Sheets

(56) References Cited

OTHER PUBLICATIONS

United States Patent and Trademark Office, Non-Final Office Action for U.S. Appl. No. 13/657,259, Jul. 24, 2014.
Wolfe et al., "Polymorphic Cocystals" Poster, AAPS Meeting (2010).
Bevill et al., "Phase Diagrams Illustrating Solubility and Gibb's Free Energy of 1:1 and 2:1 Cocrystals of Nutraceutical p-Coumaric Acid with Nicotinamide," Abstract ID: AM-12-02982 (Jun. 8, 2012).
Bevill et al., "Polymorphic Cocrystals of Nutraceutical Compound p-Coumaric Acid with Nicotinamide: Characterization, Relative Solid-State Stability, and Conversion to Alternate Stoichiometries," Cryst. Growth Des., pp. 1438-1448 (2014).
Bevill et al., "Phase Diagrams Illustrating Solubility and Gibb's Free Energy of 1:1 and 2:1 Cocrystals of Nutraceutical p-Coumaric Acid with Nicotinamide," Poster, AAPS Meeting (2012).

* cited by examiner

POLYMORPHS OF COCRYSTALS OF P-COUMARIC ACID:NICOTINAMIDE

This application claims the benefit of priority to U.S. Provisional Application No. 61/935,570, filed on Feb. 4, 2014, the entire contents of which are incorporated by reference herein.

The invention relates to polymorphs of cocrystals of p-coumaric acid and nicotinamide, pharmaceutical compositions comprising the polymorphs of the novel cocrystals, methods of making the polymorphs of the novel cocrystals, and methods of treatment with polymorphs of the novel cocrystals.

BACKGROUND

P-coumaric acid is a phytochemical and nutraceutical and is commonly found in various edible plants such as peanuts, tomatoes, and carrots. Promising pharmacokinetic studies with p-coumaric acid have shown it to have a positive response in protection against colon cancer on cultured mammalian cells. Other studies have shown it to have anti-inflammatory and antioxidant properties in animals. Nicotinamide is the amide of nicotinic acid and is a water-soluble vitamin. Nicotinamide has anti-inflammatory properties and is used in the treatment of acne.

The structures of p-coumaric acid and nicotinamide are shown below:

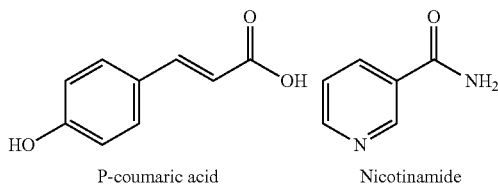

P-coumaric acid      Nicotinamide

Cocrystals of p-coumaric acid have previously been published. For example, cocrystals with caffeine and theophylline have previously been described (Cryst. Eng. Comm. 2011, 13 611-19). Likewise, cocrystals containing nicotinamide have been reported. In addition, a 1:1 cocrystal of p-coumaric acid:nicotinamide has been prepared by the inventors. The cocrystals disclosed herein are polymorphs of that cocrystal.

A cocrystal of a compound is a distinct chemical composition between the compound and coformer, and generally possesses distinct crystallographic and spectroscopic properties when compared to those of the compound and coformer individually. A coformer is also a compound and is often referred to as a "guest". The compound which is not the coformer is often referred to as the "host." Unlike salts, which possess a neutral net charge, but which are comprised of charge-balanced components, cocrystals are comprised of neutral species. Thus, unlike a salt, one cannot determine the stoichiometry of a cocrystal based on charge balance. Indeed, one can often obtain cocrystals having molar ratios of compound to coformer of greater than or less than 1:1. The molar ratio of the components is a generally unpredictable feature of a cocrystal.

Cocrystals have the potential to alter physicochemical properties. More specifically, cocrystals have been reported to alter aqueous solubility and/or dissolution rates, increase stability with respect to relative humidity, and improve bioavailability of active pharmaceutical ingredients with respect to other cocrystals of such ingredients. The coformer, or guest, is often varied or selected for purposes of altering such properties.

The chemical composition of a cocrystal, including the molar relationship between the coformer and the compound (such as an API) can be determined by single crystal x-ray analysis. Where such an analysis is not available, often solution-state proton NMR is used to verify composition and identify molar ratio.

Cocrystal formation may be further confirmed by comparing solid-state analytical data of the starting materials with the corresponding analytical method collected of the cocrystal. Data from a cocrystal will be represented by an analytical response that is not simply a linear superposition of the starting materials. For example, x-ray powder diffraction (XRPD) may be used for such comparison and the XRPD pattern of a cocrystal will differ from that of a physical mixture of the starting materials. Single crystal studies can confirm solid-state structure. In a cocrystal, the compound and the coformers each possess unique lattice positions within the unit cell of the crystal lattice. Additionally, indexing may be used to confirm the presence of a single phase.

A single crystal structure is not necessary to characterize a cocrystal. Other solid-state analytical techniques may be used to characterize cocrystals. Crystallographic and spectroscopic properties of cocrystals can be analyzed with XRPD, Raman spectroscopy infrared spectroscopy, and solid-state $^{13}C$ NMR spectroscopy, among other techniques. Cocrystals often also exhibit distinct thermal behavior compared with other forms of the corresponding compound. Thermal behavior may be analyzed by such techniques as capillary melting point, thermogravimetric analysis (TGA), and differential scanning calorimetry (DSC) to name a few. These techniques can be used to identify and characterize the cocrystals.

For example, the entire XRPD pattern output from a diffractometer may be used to characterize a cocrystal. A smaller subset of such data, however, may also be suitable for characterizing a cocrystal. For example, a collection of one or more peaks from such a pattern may be used to characterize a cocrystal. Indeed, even a single XRPD peak may be used to characterize a cocrystal. Similarly, subsets of spectra of other techniques may be used alone or in combination with other analytical data to characterize cocrystals. In such examples of characterization as provided herein, in addition to the x-ray peak data, one also is able to provide the identity of the guest and host of the cocrystal and, often, their respective molar ratio as part of the characterization.

An XRPD pattern is an x-y graph with °2θ (diffraction angle) on the x-axis and intensity on the y-axis. These are the peaks which may be used to characterize a cocrystal. The peaks are usually represented and referred to by their position on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the pharmaceutical arts to characterize cocrystals.

As with any data measurement, there is variability in x-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline cocrystal. Likewise, different software packages process x-ray data differently and this also leads to variability. These and other sources of variability are known to those of ordinary skill in the pharmaceutical arts.

Due to such sources of variability, it is common to recite x-ray diffraction peaks using the word "about" prior to the peak value in °2θ which presents the data to within 0.1 or 0.2 °2θ of the stated peak value depending on the circumstances. All x-ray powder diffraction peaks cited herein are reported with a variability on the order of 0.2 °2θ and are intended to be reported with such a variability whenever disclosed herein whether the word "about" is present or not.

Thermal methods are another typical technique to characterize cocrystals. Different cocrystals of the same compound often melt at different temperatures. Variability also exists in thermal measurements and may also be indicative of sample purity. Melting point, such as measured by differential scanning calorimetry (DSC) and thermal microscopy, alone or in combination with techniques such as x-ray powder diffraction, may be used to characterize cocrystals.

As with any analytical technique, melting point determinations are also subject to variability. Common sources of variability, in addition to instrumental variability, are due to colligative properties such as the presence of other cocrystals or other impurities within a sample whose melting point is being measured.

SUMMARY

In one aspect of the invention, a cocrystal of p-coumaric acid to nicotinamide in a 1:1 molar ratio is disclosed referred to as Form II. In a further aspect of the invention, another cocrystal of p-coumaric acid to nicotinamide in a molar ratio of 1:1 is disclosed and is referred to as Form III. In further aspects, pharmaceutical compositions comprising one or both of the cocrystals described herein are described. In yet further aspects, methods of treating conditions treatable by administration of the cocrystals described herein are disclosed as are processes for making such cocrystals.

DESCRIPTION

Figure 1:
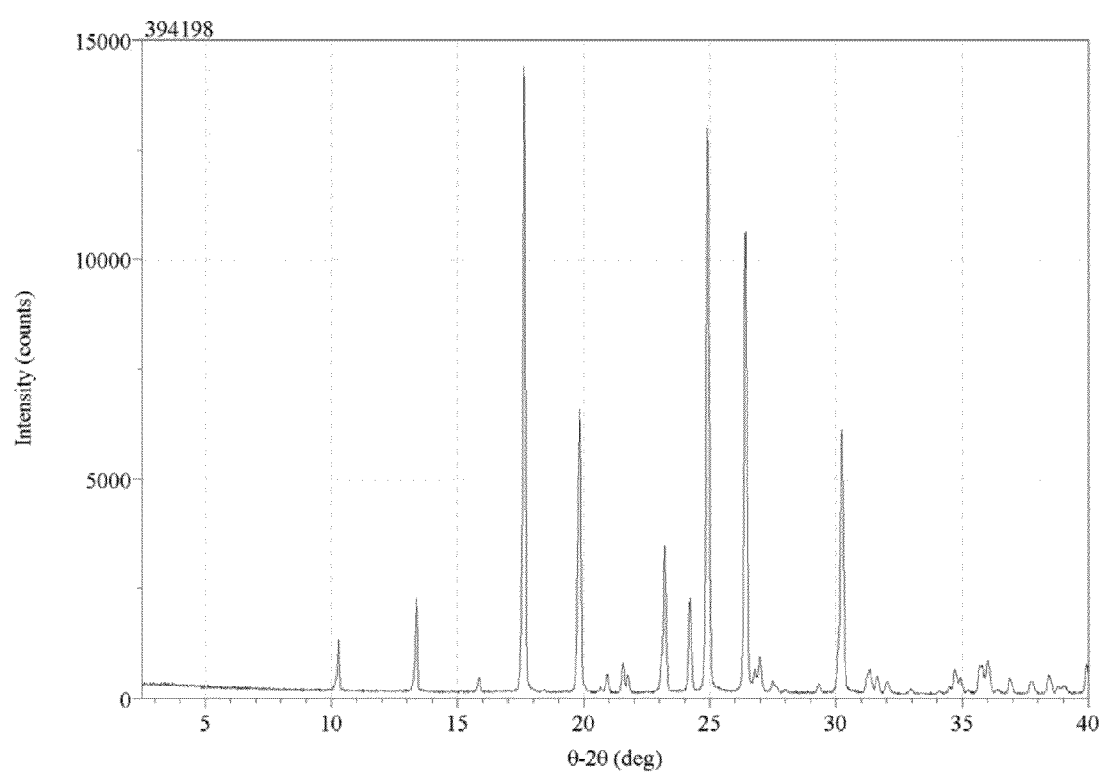
FIG. 1 is an XRPD pattern of p-coumaric acid.

The XRPD pattern corresponding to the p-coumaric acid starting material used herein is in FIG. 1. The XRPD pattern of the nicotinamide starting material is in FIG. 2. The XRPD pattern for the resulting Form II is in FIG. 3.

Figure 2:
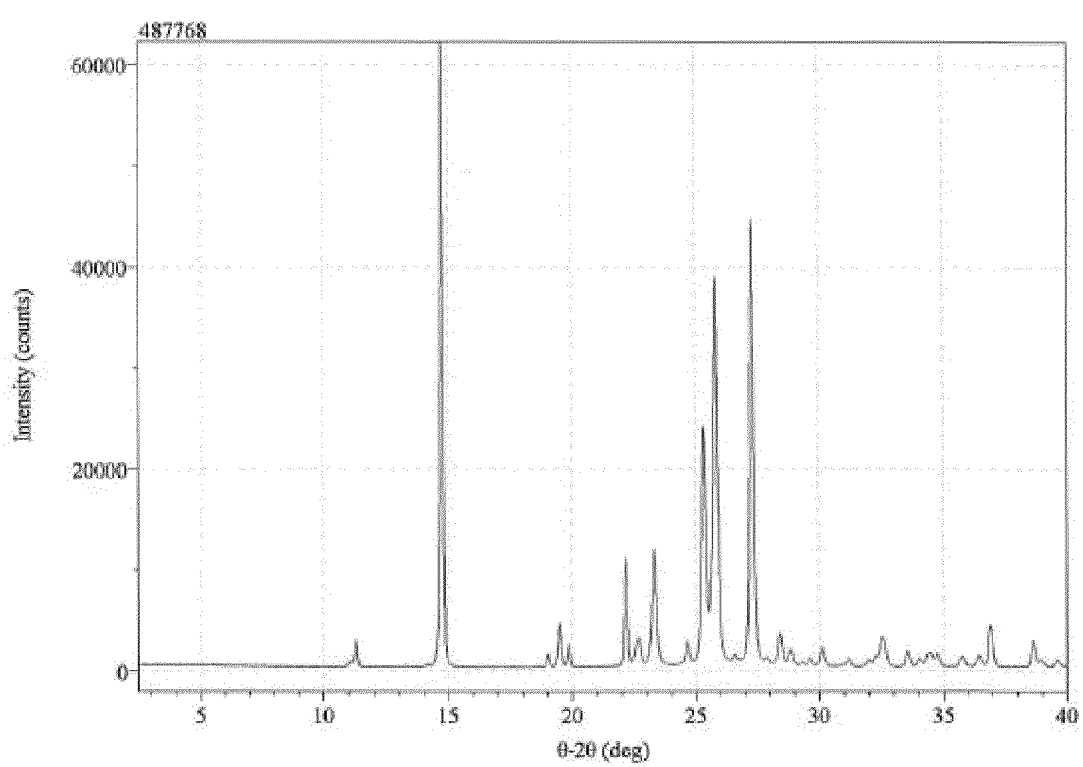
FIG. 2 is an XRPD pattern of nicotinamide.
Figure 3:
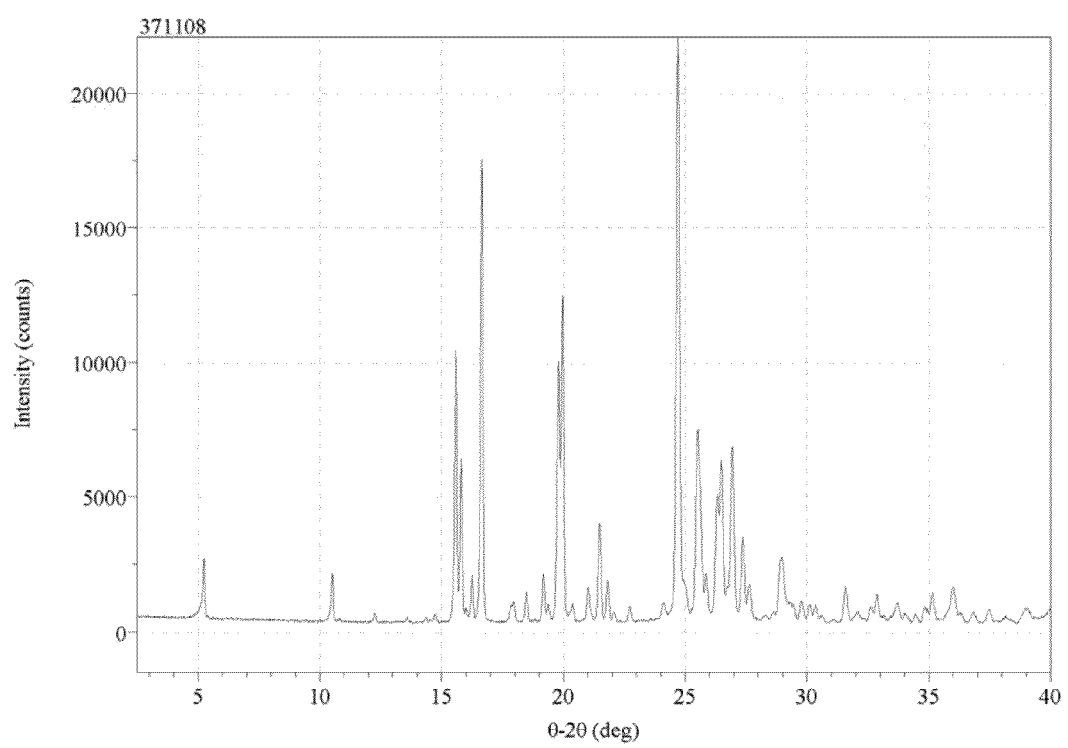
FIG. 3 is an XRPD pattern of Form II.
Figure 4:
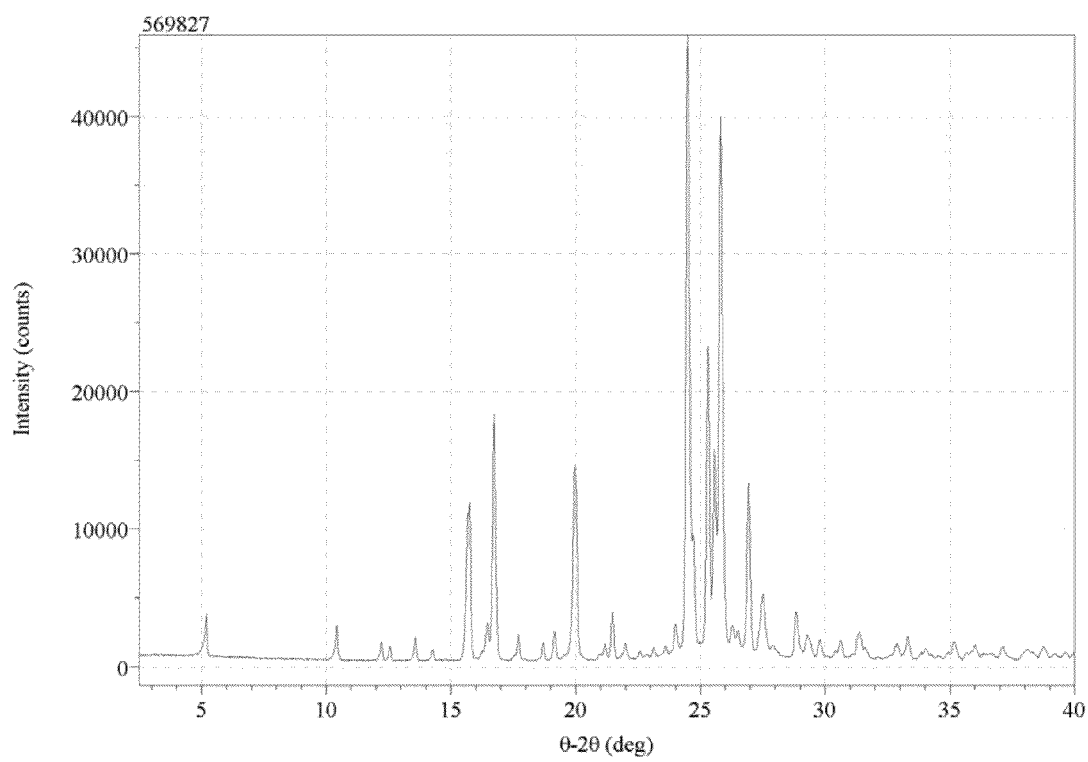
FIG. 4 is an XRPD pattern of Form III (with minor component being Form II).

As can be readily determined, the XPRD pattern of FIGS. 3 and 4 respectively differ from those of FIGS. 1 and 2, and, therefore, Forms II and III not merely a linear superposition of the patterns. Rather, these data prove that the cocrystals of Forms II and III are not mixtures of starting materials but are distinct compositions of matter.

In one embodiment of the invention, Form II of a cocrystal of p-coumaric acid to nicotinamide in a molar ratio of 1:1 is disclosed. In another embodiment of the invention, Form III of a cocrystal of p-coumaric acid to nicotinamide in a molar ratio of 1:1 is disclosed. In additional embodiments, pharmaceutical compositions of Forms II, III, or both are described herein. Other embodiments include processes for making Forms II or III and still further embodiments include methods of treating diseases such as inflammation with Forms II or III or both.

Form I of a cocrystal of p-coumaric acid to nicotinamide in a molar ratio of 1:1 has previously been disclosed and claimed in US 2014/0073674. Forms I, II, and III of the 1:1 cocrystal of p-coumaric acid and nicotinamide are polymorphs of one another. Polymorphs of a compound share the same chemical formula but differ in crystalline structure. The differences in chemical structure may be identified by reference to any one of a number of analytical techniques. These techniques may be used to distinguish polymorphs from one another and, therefore, may be used to characterize the polymorphs.

The different polymorphic forms of the 1:1 cocrystal of p-coumaric acid:nicotinamide may be characterized by a number of different analytical techniques. For example, Form I may be distinguished from both Forms II and III by melting point alone. The onset melting point of Form I as measured by DSC and confirmed by thermomicroscopy as disclosed herein is 154° C. whereas Forms II and III under the same conditions melt at about 158° C. and about 160° C. respectively. Further, Form I exhibits peaks in the x-ray XRPD pattern, as measured under similar experimental conditions as Forms II and III, at about 5.9 and 11.8 degrees two theta. Neither Form II nor Form III have peaks within typical experimental variation of those two peaks. Thus, either one of those peaks, together with or separate from melt onset as measured herein at about 154° C. can distinguish Form I from Forms II or III.

Figure 5:
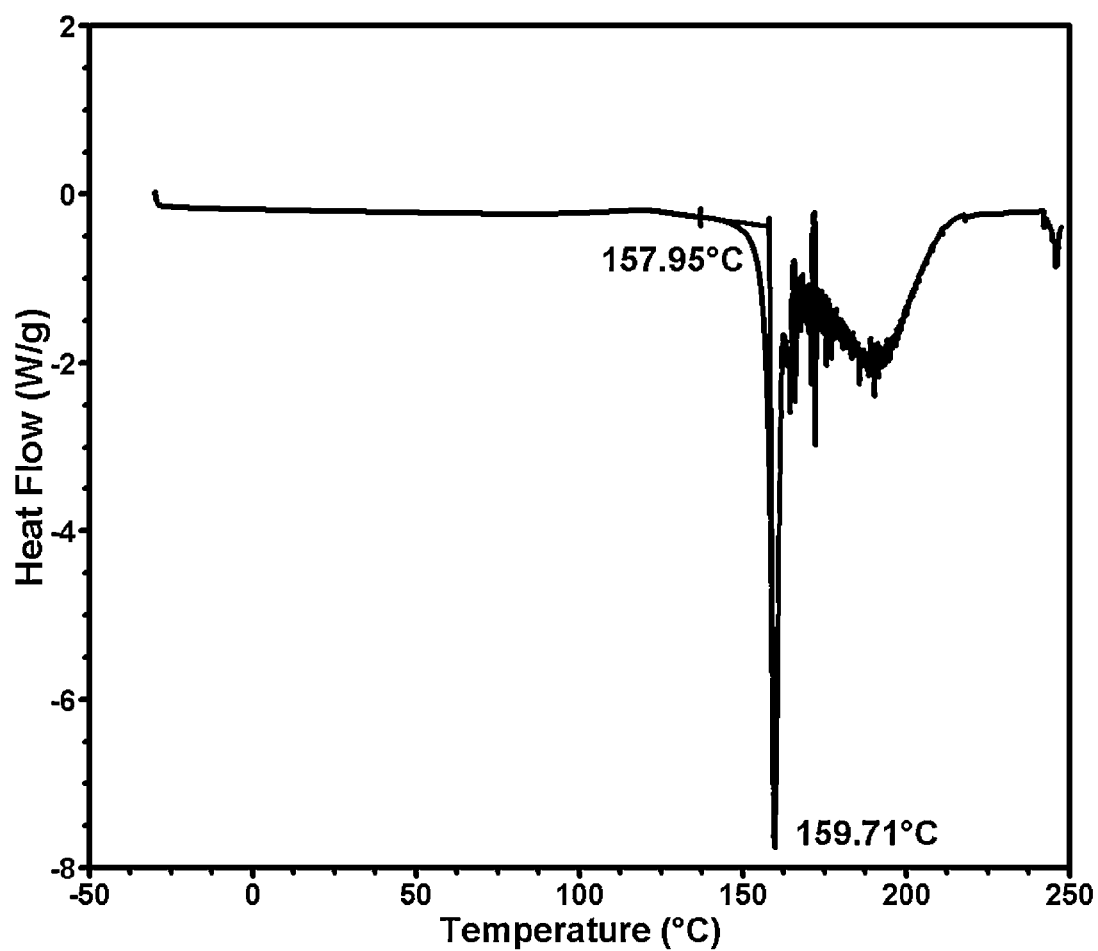
FIG. 5 is a DSC Thermogram of Form II.
Figure 6:
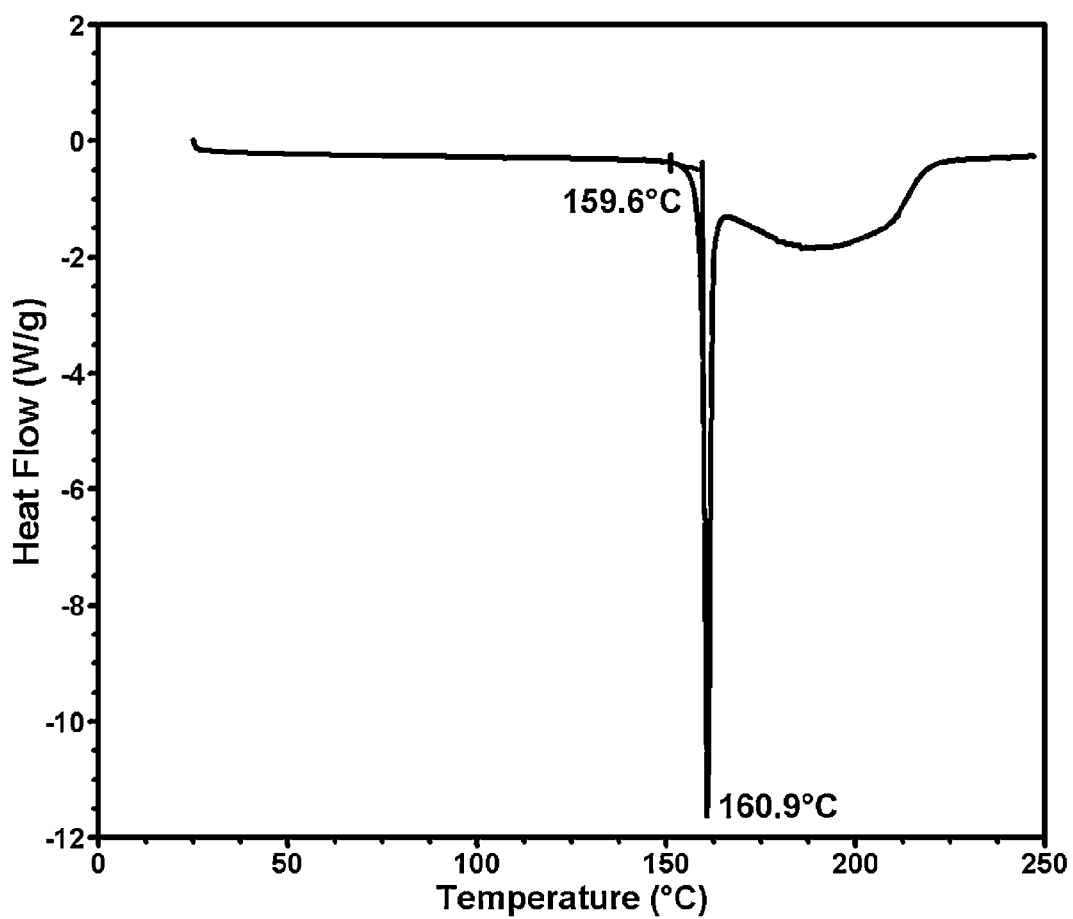
FIG. 6 is a DSC Thermogram of Form III (with a minor component being Form II)

Forms II and III may be further distinguished from each other by both thermal measurements and by XRPD peaks. The melting point differences of about 158° C. and about 160° C. for Forms II and III respectively are sufficient to characterize the forms. These melting points are determined by a combination of DSC and thermomicroscopy. For example, FIG. 5, a DSC thermogram of Form II, illustrates an endotherm onset occurring at about 158° C. Thermomicroscopy confirms that this endotherm is a melt. FIG. 6 is a DSC thermogram of Form III (with a minor component of Form II), which by DSC and thermomicroscopy shows an endotherm onset which is a melt occurring at about 160° C.

The forms may also be characterized by XRPD. For example, as seen in FIGS. 3 and 4, Form II exhibits a peak in its XRPD pattern, as set forth herein, at about 26.3 °2θ whereas Form III exhibits a peak at about 25.8 °2θ. Either single peak alone, or in combination with the onset melting temperature, suffices to characterize each of Form II and Form III. In addition, Form II exhibits two peaks at between about 15.4 °2θ and 16.0 °2θ (about 15.6 °2θ and 15.8 °2θ) degrees two theta whereas Form III only has one peak in that range (about 15.7 °2θ). Thus, the presence of only one peak between about 15.4 °2θ and about 16.0 °2θ alone characterizes Form III. The presence of a single peak between about 15.4 °2θ and about 16.0 °2θ together with a peak at about 25.8 °2θ and/or the melting onset of about 160° C. may be used to characterize Form III. By comparison, the presence of two peaks between about 15.4 °2θ and about 16.0 °2θ may be used to characterize Form II or these two peaks in combination with a peak at about 26.3 °2θ and/or a melting onset of 158° C. may be used to characterize Form II.

By "peak" as used herein what is meant is a signal that is not noise and which represents a reflection in the x-ray powder diffraction pattern. Those of ordinary skill in the art recognize that some peaks are susceptible to preferred orientation or particle statistical affects. The fact that a peak may not be visible due to these affects does not mean the peak is not present in the material. Thus, to rule out the presence of a peak other than due to such artifacts, it may be necessary to run replicate samples of the materials analyzed.

This invention also relates to pharmaceutical compositions containing Form II or Form II of the present invention. These compositions can be utilized to achieve the desired pharmacological effect by administration to a patient in need thereof including, treatment of acne or other inflammation conditions. A patient, for the purpose of this invention, is a mammal, including a human, in need of treatment for the particular condition or disease including, but not limited to, acne or other inflammation conditions. Therefore, the present invention includes pharmaceutical compositions which are comprised of at least one pharmaceutically acceptable carrier and one or more of Form II or Form III of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compound of Form II or Form III or both of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

EXAMPLES

All chemicals were obtained from commercial sources and used without further purification.

Patterns were collected using a PANalytical X'Pert Pro MPD X-ray diffractometer. An incident beam of Cu radiation was produced using an Optix long, fine-focus source. An elliptically graded multilayer mirror was used to focus Cu Kα X-rays through the specimen and onto the detector. The sample was prepared by sandwiching a portion of the solids between 3-μm thick films and analyzing in transmission geometry. A beam-stop, short antiscatter extension, and an antiscatter knife edge were used to minimize the background generated by air. Soller slits for the incident and diffracted beams were used to minimize broadening from axial divergence. PANalytical data were collected using a scanning position-sensitive detector (X'Celerator) located 240 mm from the specimen and Data Collector software v. 2.2b. Prior to the analysis, a silicon specimen (NIST SRM 640c or 640d) was analyzed to verify the Si 111 peak position.

Solution $^1$H NMR spectra were acquired at ambient temperature with a Varian$^{UNITY}$ INOVA-400 spectrometer at a $^1$H Larmor frequency of 399.796 or 399.798 MHz. Each sample was dissolved in DMSO-$d_6$ containing tetramethylsilane (TMS). The spectra were acquired with the following parameters: 6-9 μs $^1$H pulse width; 2.50 or 5.00 second acquisition time; 5.00 or 2.50 second delay between scans; 6400 or 7000 Hz spectral width; 31998, 35000, or 64000 data points; and 40 co-added scans. Each free induction decay (FID) was processed with 64000, 131072, or 262144 points and an exponential line broadening factor of 0.2 Hz to improve the signal-to-noise ratio. The spectra were referenced to internal TMS at 0.0 ppm. Stoichiometry was confirmed for all cocrystals by $^1$H NMR spectroscopy, and only minor amounts of residual organic solvents were present based on the spectra for each cocrystal. The samples were not vacuum dried prior to characterization, which would leave residual process solvents.

DSC was performed using a TA Instruments Q2000 differential scanning calorimeter. Temperature calibration was performed using NIST-traceable indium metal. Each sample was placed into an aluminum DSC pan or a Tzero pan, covered with a lid, the lid was crimped, and the weight was accurately recorded. A weighed aluminum pan configured as the sample pan was placed on the reference side of the cell. Each sample was heated using a heating rate of 10° C. per minute from either −30° C. or 25° C. up to 250° C.

Thermomicroscopy was performed using a Linkam hot stage (FTIR 600) mounted on a Leica DM LP microscope equipped with a SPOT Insight™ color digital camera. The sample was placed on a cover glass with another cover glass placed on top. As the stage was heated, each sample was visually observed using a 20×0.40 numerical aperture long working distance objective with crossed polarizers and a first order red compensator. Images were captured using SPOT software (v. 4.5.9). Temperature calibrations were performed using USP melting point standards.

Example 1

Form II Preparation

Weighed amounts of p-coumaric acid (304.0 mg) and nicotinamide (226.1 mg) were added to a clean vial in a 1:1 molar ratio. Tetrahydrofuran (20 mL) was added with sonication, resulting in a clear solution. The solution was uncapped and covered with perforated aluminum foil for slow evaporation at ambient conditions. After approximately 2 weeks, the sample contained solids with a very small amount of solvent remaining. The solids were collected by vacuum filtration and washed with tetrahydrofuran on the filter. Other crystallization techniques that produced Form II include cooling, evaporation, vapor diffusion, and slurrying with one component in molar excess, all in a variety of solvents such as ethyl acetate, p-dioxane, 2-propanol, and/or methyl ethyl ketone. An x-ray powder diffractogram of a sample made according to Example 1 can be found in FIG. 3.

Example 2

Form III Preparation

Single crystals of Form III were produced from a vapor diffusion experiment. A bulk solution of p-coumaric acid (102.7 mg, 0.6 mmol) and nicotinamide (76.6 mg, 0.6 mmol) in a 1:1 molar ratio was prepared in ethanol (3 mL). A small amount of this solution (550 μL) was added to a 1-dram vial, which was placed inside a 20-mL vial containing nitromethane (2 mL). The 20-mL vial was capped for vapor diffusion at ambient conditions. After 3 weeks, single crystals of Form III were harvested, although analysis of the solids by XRPD indicated concomitant crystallization of Form III and Form II. While multiple crystallization techniques, such as cooling, evaporation, and vapor diffusion, utilizing a variety of solvents, produced mixtures of Form III with Form II and/or Form I, only one slow evaporation experiment in ethanol yielded Form III primarily in a single phase with only a minor amount of Form II present by XRPD. An x-ray powder diffractogram of Form III with a minor amount of Form II is present in FIG. 4. A single crystal structure solution was performed on Form III with a summary of the results to be found in Table 1. A calculated XRPD pattern was generated on the single crystal data represented in Table 1 and was compared with an experimental pattern of Form III prepared by an ethanol slow evaporation technique. In the experiment corresponding to that slow evaporation technique, p-coumaric acid (99.9 mg) was combined with nicotinamide (76.1 mg) and the mixture was dissolved in ethanol and allowed to slowly evaporate at ambient conditions. A shoulder on a peak can be seen at about 24.7 °2θ and a small doublet between about 26.2 and 26.6 °2θ are present in the experimental pattern but not in the calculated pattern. Further, this shoulder and double align with peaks in Form II. However, based on peak intensities, the Form II component is minor.

TABLE 1

| Empirical formula | $C_{15}H_{14}N_2O_4$ | |
|---|---|---|
| Formula weight | 286.28 | |
| Temperature | 120(2) K | |
| Wavelength | 0.71073 Å | |
| Crystal system | Monoclinic | |
| Space group | C2/c | |
| Unit cell dimensions | a = 40.076(2) Å | α = 90°. |
| | b = 7.1979(4) Å | β = 122.479(2)°. |
| | c = 22.2876(12) Å | γ = 90°. |
| Volume | 5423.5(5) Å$^3$ | |
| Z | 16 | |
| Density (calculated) | 1.402 g/cm$^3$ | |
| Absorption coefficient | 0.103 mm$^{-1}$ | |
| F(000) | 2400 | |
| Crystal size | 0.34 × 0.14 × 0.12 mm$^3$ | |
| Theta range for data collection | 1.83 to 31.00°. | |
| Index ranges | −58 <= h <= 58, −10 <= k <= 6, −20 <= l <= 32 | |

TABLE 1-continued

| Reflections collected | 30156 |
|---|---|
| Independent reflections | 8438 [R(int) = 0.0406] |
| Completeness to theta = 31.00° | 97.5% |
| Absorption correction | None |
| Max. and min. transmission | 0.9877 and 0.9657 |
| Refinement method | Full-matrix least-squares on F$^2$ |
| Data/restraints/parameters | 8438/0/403 |
| Goodness-of-fit on F$^2$ | 1.084 |
| Final R indices [I > 2sigma(I)] | R1 = 0.0537, wR2 = 0.1346 |
| R indices (all data) | R1 = 0.0887, wR2 = 0.1492 |
| Largest diff. peak and hole | 0.506 and −0.257 e.Å$^{-3}$ |

We claim:

1. Form II of a 1:1 cocrystal of p-coumaric acid and nicotinamide, wherein the x-ray powder diffraction pattern does not have a peak at about 5.9 °2θ.

2. The cocrystal of claim 1 having an x-ray powder diffraction pattern comprising a peak at about 26.3 °2θ.

3. The cocrystal of claim 2 wherein the x-ray powder diffraction pattern further comprises two peaks between about 15.4 °2θ and 16.0 °2θ.

4. The cocrystal of claim 1 having a melting onset temperature of about 158° C.

5. The cocrystal of claim 1 having an x-ray powder diffraction pattern comprising a peak at about 26.3 °2θ and two peaks between about 15.4 and 16.0 °2θ.

6. The cocrystal of claim 5 having a melting onset temperature of about 158° C.

7. A pharmaceutical composition comprising at least one cocrystal of claim 1 and at least one pharmaceutically acceptable carrier.

8. The pharmaceutical composition of claim 7 wherein at least one cocrystal is in a pharmaceutically effective amount.

* * * * *